United States Patent
Iwakuni et al.

(10) Patent No.: US 12,378,116 B2
(45) Date of Patent: Aug. 5, 2025

(54) TITANIUM PHOSPHATE POWDER, PRODUCTION METHOD THEREFOR, AND WHITE PIGMENT FOR COSMETICS

(71) Applicant: FUJIMI INCORPORATED, Kiyosu (JP)

(72) Inventors: Mayumi Iwakuni, Kiyosu (JP); Keiji Ashitaka, Kiyosu (JP); Naoya Miwa, Kiyosu (JP)

(73) Assignee: FUJIMI INCORPORATED, Kiyosu (JP)

( * ) Notice: Subject to any disclaimer, the term of this patent is extended or adjusted under 35 U.S.C. 154(b) by 781 days.

(21) Appl. No.: 17/585,134

(22) Filed: Jan. 26, 2022

(65) Prior Publication Data
US 2022/0144639 A1  May 12, 2022

Related U.S. Application Data

(62) Division of application No. 16/498,140, filed as application No. PCT/JP2018/011098 on Mar. 20, 2018, now Pat. No. 11,345,596.

(30) Foreign Application Priority Data

Mar. 30, 2017  (JP) ................. 2017-068350

(51) Int. Cl.
  *C01B 25/37*  (2006.01)
  *A61K 8/29*  (2006.01)
(52) U.S. Cl.
  CPC .............. *C01B 25/372* (2013.01); *A61K 8/29* (2013.01); *A61K 2800/412* (2013.01);
  (Continued)
(58) Field of Classification Search
  None
  See application file for complete search history.

(56) References Cited

U.S. PATENT DOCUMENTS

| 3,556,720 | A | 1/1971 | Cox |
| 3,558,273 | A | 1/1971 | Beck |

(Continued)

FOREIGN PATENT DOCUMENTS

| CN | 101033062 A | 9/2007 |
| CN | 102641214 A | 8/2012 |

(Continued)

OTHER PUBLICATIONS

International Search Report with English translation and Written Opinion issued in corresponding application No. PCT/JP2018/011098 dated Jun. 19, 2018.

(Continued)

*Primary Examiner* — Coris Fung
*Assistant Examiner* — Jialan Zhang
(74) *Attorney, Agent, or Firm* — Foley & Lardner LLP

(57) ABSTRACT

The titanium phosphate powder of the present invention includes plate-shaped crystalline particles of titanium phosphate, an average thickness of the plate-shaped crystalline particles is 0.01 μm or more and less than 0.10 μm, and an aspect ratio, which is a value obtained by dividing an average primary particle diameter of the plate-shaped crystalline particles by the average thickness, is 5 or more. In the method for producing a titanium phosphate powder of the present invention, a raw material containing titanium and phosphorus is caused to react by a hydrothermal synthesis method, and when the titanium phosphate powder including plate-shaped crystalline particles of titanium phosphate is produced, a mixture of titanium sulfate and phosphoric acid is used as the raw material.

15 Claims, 4 Drawing Sheets

(52) U.S. Cl.
CPC ...... *A61K 2800/43* (2013.01); *C01P 2004/20* (2013.01); *C01P 2004/54* (2013.01); *C01P 2004/62* (2013.01)

(56) References Cited

U.S. PATENT DOCUMENTS

| | | | |
|---|---|---|---|
| 3,914,381 | A | 10/1975 | Sugahara |
| 2008/0159940 | A1 | 7/2008 | Aupaix |
| 2013/0209387 | A1 | 8/2013 | Pappas et al. |
| 2013/0224140 | A1 | 8/2013 | Pappas et al. |
| 2014/0044971 | A1 | 2/2014 | Sueda et al. |
| 2014/0050925 | A1 | 2/2014 | Sueda et al. |
| 2014/0058029 | A1 | 2/2014 | Sueda et al. |
| 2014/0112862 | A1 | 4/2014 | Sueda et al. |
| 2015/0328097 | A1 | 11/2015 | Pappas et al. |
| 2017/0008773 | A1 | 1/2017 | Pappas et al. |
| 2020/0377369 | A1 | 12/2020 | Iwakuni et al. |
| 2021/0145712 | A1 | 5/2021 | Iwakuni et al. |

FOREIGN PATENT DOCUMENTS

| | | | | |
|---|---|---|---|---|
| EP | 3 604 218 | A1 | 2/2020 | |
| EP | 3 777 819 | A1 | 2/2021 | |
| GB | 1282594 | A * | 7/1972 | ............. B82Y 30/00 |
| JP | S49-1720 | B1 | 1/1974 | |
| JP | S49-019520 | B1 | 5/1974 | |
| JP | H10-046135 | A | 2/1998 | |
| JP | H10-167929 | A | 6/1998 | |
| JP | 2005-505669 | A | 2/2005 | |
| JP | 2005-089214 | A | 4/2005 | |
| JP | 2007-291090 | A | 11/2007 | |
| JP | 2008-503436 | A | 2/2008 | |
| JP | 2008-056535 | A | 3/2008 | |
| JP | 4649102 | B2 | 12/2010 | |
| JP | 4684970 | B1 | 5/2011 | |
| JP | 2013-095888 | A | 5/2013 | |
| SU | 1611906 | A | 12/1990 | |
| WO | WO-2012/061280 | A2 | 5/2012 | |
| WO | WO-2012/147888 | A1 | 11/2012 | |
| WO | WO-2018/180797 | A1 | 10/2018 | |
| WO | WO-2019/189665 | A1 | 10/2019 | |
| WO | WO-2020/059190 | A1 | 3/2020 | |
| WO | WO-2020/059191 | A1 | 3/2020 | |

OTHER PUBLICATIONS

English translation of the International Preliminary Report on Patentability issued in corresponding application No. PCT/JP2018/011098 dated Oct. 10, 2019.
Onoda et al., "Preparation of titanium phosphate white pigments with titanium sulfate and their powder properties", Journal of Advanced Ceramics, 3(2): 2014, 132-136.
Guo et al., "Synthesis of shape-controlled mesoporous titanium phosphate nanocrystals: The hexagonal titanium phosphate with enhanced hydrogen generation from water splitting", International Journal of Hydrogen, Energy, Elsevier Science Publishers B.V., Barking, GB, vol. 39, No. 6, Dec. 25, 2013 (Dec. 25, 2013), XP028828982, pp. 2446-2453.
Office Action issued in corresponding European Patent Application No. 19777809.5, dated Mar. 22, 2023 (8 pages).
US Non-Final Office Action on U.S. Appl. No. 17/043,166 dated Apr. 25, 2023 (10 pages).
U.S. Appl. No. 17/276,288, filed Mar. 15, 2021, Iwakuni et al.
U.S. Appl. No. 17/276,299, filed Mar. 15, 2021, Iwakuni et al.
English translation of the International Preliminary Report on Patentability issued in corresponding PCT Application No. PCT/2019/013799, dated Apr. 1, 2021.
English translation of the International Preliminary Report on Patentability issued in corresponding PCT Application No. PCT/2019/013800, dated Apr. 1, 2021.
Extended European Search Report issued in corresponding European Application No. 19862261.5 dated Oct. 13, 2021.
Extended European Search Report issued in corresponding European Application No. 19862336.5 dated Oct. 15, 2021.
Extended European Search Report issued in corresponding European Patent Application No. 19777809.5 dated May 7, 2021.
Extended European Search Report issued in European Patent Application No. 21214767.2 dated Mar. 23, 2022.
Non-Final Office Action on U.S. Appl. No. 17/043,166 Dtd May 24, 2022.
Non-Final Office Action on U.S. Appl. No. 17/276,288 Dtd Mar. 31, 2022.
Non-Final Office Action on U.S. Appl. No. 17/276,299 Dtd Mar. 31, 2022.
Notice of Allowance on U.S. Appl. No. 16/498,140 Dtd Feb. 2, 2022.
Onoda et al., "Influence of Temperature and ultrasonic Treatment on Preparation of Titanium Phosphates and Their Powder Properties", Cosmetics, vol. 1, 2014, pp. 222-231.
Onoda et al., "Mechanical Treatment on Powder Properties of Titanium Phosphate White Pigments", Phosphorus Research Bulletin, vol. 29, 2014, pp. 006-010.
Onoda, et al., "Influence of concentration in phosphoric acid treatment of titanium oxide and their powder properties", Journal of Asian Ceramic Societies, vol. 3, No. 1, 2015, pp. 27-31.
Onoda, et al., "Preparation of titanium phosphates with additives in hydrothermal process and their powder properties for cosmetics", International Journal of Cosmetic Science, 2013, 35, pp. 196-200.
US Notice of Allowance on US Appl. U.S. Appl. No. 17/276,288 dated Dec. 22, 2022 (7 pages).
US Final Office Action on US Appl. U.S. Appl. No. 17/043,166 dated Sep. 26, 2022 (9 pages).
US Final Office Action on US Appl. U.S. Appl. No. 17/276,288 dated Oct. 20, 2022 (10 pages).
US Final Office Action on US Appl. U.S. Appl. No. 17/276,299 dated Oct. 20, 2022 (13 pages).
US Non-Final Office Action for US Appl. U.S. Appl. No. 18/456,072 dated May 22, 2024 (8 pages).

* cited by examiner

TITANIUM PHOSPHATE POWDER, PRODUCTION METHOD THEREFOR, AND WHITE PIGMENT FOR COSMETICS

CROSS REFERENCE TO RELATED APPLICATIONS

The present application is a divisional of U.S. patent application Ser. No. 16/498,140, filed on Sep. 26, 2019, which is a national stage entry of PCT/JP2018/011098, filed Mar. 20, 2018, which claims the benefit of priority to Japanese Patent Application No. 2017-068350 filed on Mar. 30, 2017, the entire contents of all of which are incorporated herein by reference.

TECHNICAL FIELD

The present invention relates to a titanium phosphate powder, a production method therefor, and a white pigment for cosmetics.

BACKGROUND ART

As a titanium phosphate powder, one composed of amorphous titanium phosphate (for example, see PTL 1) and one composed of plate-shaped crystalline particles of titanium phosphate (for example, see PTL 2) are disclosed.

PTL 1 describes the use of, as an ultraviolet blocking agent, amorphous phosphate of Ce and/or Ti, containing one or more elements of B, Al, Si, Zn, Ga, Zr, Nb, Mo, Ta, and W as a crystallization inhibiting component. PTL 1 further describes that the ultraviolet blocking agent is amorphous phosphate having excellent heat resistance, and suitable applications of the ultraviolet blocking agent include a cosmetic product, a resin molded article, a paint, and the like.

PTL 2 describes a method of producing a titanium phosphate powder composed of plate-shaped crystalline particles of titanium phosphate by causing a raw material containing titanium and phosphorus to react by a hydrothermal synthesis method. PTL 2 further describes that plate-shaped crystalline particles of titanium phosphate, corresponding to the structural formula of $Ti(HPO_4)_2H_2O$ are obtained by this method.

As a specific example, PTL 2 describes that hexagonal plate-shaped crystalline particles of titanium phosphate, having a particle diameter of 0.25 to 0.5 μm and 0.4 to 0.7 μm and a thickness of 0.1 to 0.2 μm are obtained. PTL 2 further describes that the obtained plate-shaped crystalline particles of titanium phosphate are useful as a reinforcing agent of a building material, a pigment of a paint, and the like.

PTL 2 does not describe an example of using a mixture of titanium sulfate and phosphoric acid as a raw material in the method for producing a titanium phosphate powder composed of plate-shaped crystalline particles of titanium phosphate.

CITATION LIST

Patent Literatures

PTL 1: JP 4649102 B2
PTL 2: JP S49-1720 A

SUMMARY OF INVENTION

Technical Problem

As mentioned above, in the case where the powder is an additive, a pigment, or the like which is used by adding it to cosmetics, a paint, and the like, each of particles constituting the powder preferably has a thin plate shape because slipperiness among particles becomes favorable.

However, the method described in PTL 2 is susceptible to improvement in terms of obtaining a powder suitable for applications such as additives and pigments.

An object of the present invention is to provide a powder suitable for applications such as additives and pigments.

Solution to Problem

The titanium phosphate powder according to one aspect of the present invention is a titanium phosphate powder that includes plate-shaped crystalline particles of titanium phosphate, wherein an average thickness of the plate-shaped crystalline particles is 0.01 μm or more and less than 0.10 μm, and an aspect ratio that is a value obtained by dividing an average primary particle diameter of the plate-shaped crystalline particles by the average thickness is 5 or more.

The method for producing a titanium phosphate powder according to one aspect of the present invention is a method for producing a titanium phosphate powder including plate-shaped crystalline particles of titanium phosphate, the method including causing a raw material containing titanium and phosphorus to react by a hydrothermal synthesis method, wherein the raw material is a mixture of titanium sulfate and phosphoric acid.

Advantageous Effects of Invention

The titanium phosphate powder of the present invention can be suitably used as an additive, a pigment, or the like.

According to the method for producing a titanium phosphate powder of the present invention, a powder suitable for applications such as additives and pigments can be obtained.

DESCRIPTION OF EMBODIMENT

Figure 1:
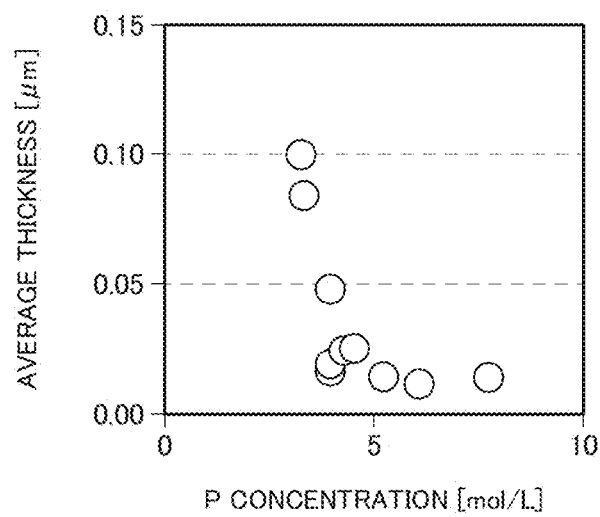
FIG. 1 is a graph illustrating a relationship between the concentration of phosphorus in a mixture of titanium(IV) sulfate and phosphoric acid and the average thickness of hexagonal plate-shaped crystalline particles of titanium phosphate, obtained from the results of Production Examples 1 to 10.

An embodiment of the present invention will be described in detail below. The following embodiment merely shows an example of the present invention, and the present invention is not limited to the present embodiment. Various variations and modifications can be made to the following embodiment, and embodiments with such variations and modifications can be included in the scope of the present invention.

The titanium phosphate powder according to the present embodiment includes plate-shaped crystalline particles of titanium phosphate. The average thickness of the plate-shaped crystalline particles is 0.01 μm or more and less than 0.10 μm, and an aspect ratio, which is a value obtained by dividing the average primary particle diameter of the plate-shaped crystalline particles by the average thickness, is 5 or more.

An average primary particle diameter of the plate-shaped crystalline particles of titanium phosphate is not particularly limited and can be 0.05 μm or more and 1.5 μm or less. The plate-shaped crystalline particles of titanium phosphate may be hexagonal plate-shaped crystalline particles.

The titanium phosphate powder according to the present embodiment is a titanium phosphate powder including thin plate-shaped crystalline particles having a high aspect ratio, which is a value obtained by dividing the particle diameter by the thickness, and a thickness of less than 0.1 μm (i.e., particles of titanium phosphate each having a shape controlled to be a thin plate shape). Thus, slipperiness among particles of titanium phosphate is favorable.

Therefore, the titanium phosphate powder according to the present embodiment is suitable as an additive added to a cosmetic agent such as a sunscreen cosmetic agent or a pigment added to a paint. The titanium phosphate powder according to the present embodiment is also suitable as a white pigment for cosmetics.

The titanium phosphate powder according to the present embodiment can be produced by causing a raw material containing titanium and phosphorus to react by a hydrothermal synthesis method. This raw material is a mixture of titanium sulfate (Ti(SO$_4$)$_2$) and phosphoric acid (H$_3$PO$_4$). The use of titanium sulfate as a titanium source facilitates the formation of thin plate-shaped crystalline particles of titanium phosphate having a higher aspect ratio.

The reaction conditions of the hydrothermal synthesis method are not particularly limited. However, the reaction temperature can be 100° C. or more and 160° C. or less. When the reaction temperature is 160° C. or less, a reaction vessel made of a glass lining material can be used in production of titanium phosphate powder, and the titanium phosphate powder can be produced by a general-purpose facility. Thus, the production cost can be reduced.

When the reaction temperature is 160° C. or less, the titanium phosphate powder can be produced in a first-class pressure vessel (pressure: 1 MPa or less). Further, when the temperature is 160° C. or less, the chemical concentration in production of titanium phosphate powder can be set under a wider range of conditions. On the other hand, when the reaction temperature is 100° C. or more, highly-crystalline plate-shaped crystalline particles of titanium phosphate can be easily obtained, and further, the titanium phosphate powder can be produced by a simple production facility because the viscosity of the product is low.

If the reaction temperature is 100° C. or less, the crystallinity of the plate-shaped crystalline particles of titanium phosphate may be slightly reduced, and the viscosity of the product may be slightly increased, which may affect the design of the production facility. Therefore, it is more preferable that the reaction temperature be 110° C. or more and 160° C. or less. In the reaction temperature range of 100° C. or more and 160° C. or less, there is no significant difference in the crystallinity of the plate-shaped crystalline particles of titanium phosphate.

The ratio [P]/[Ti] of the concentration [P] of phosphorus by mole to the concentration [Ti] of titanium by mole in the raw material may be 3 or more and 21 or less. When the ratio [P]/[Ti] is 3 or more, preferably 5 or more, plate-shaped crystalline particles of titanium phosphate are easily generated. On the other hand, in the case where the concentration of titanium in the raw material is the same, the larger the ratio [P]/[Ti] is, the smaller the average primary particle diameter of the plate-shaped crystalline particles of titanium phosphate tends to be, but even if the ratio [P]/[Ti] exceeds 21, further reduction in average primary particle diameter does not occur, and the average primary particle diameter is almost constant.

The concentration of titanium in the raw material may be 0.05 mol/L or more and 1.0 mol/L or less. When the ratio [P]/[Ti] is the same, the higher the concentration of titanium in the raw material is, the smaller the average primary particle diameter and the average secondary particle diameter of the plate-shaped crystalline particles of titanium phosphate tend to be. Further, by increasing the concentration of titanium in the raw material, the production cost can be reduced. Therefore, the concentration of titanium in the raw material is preferably 0.05 mol/L or more, more preferably 0.2 mol/L or more. However, if the concentration of titanium in the raw material is too high, the viscosity of the product may increase, and the uniformity of the product may decrease, so that the concentration of titanium in the raw material is preferably 1.0 mol/L or less, more preferably 0.6 mol/L or less.

PRODUCTION EXAMPLES

The present invention will be described in further detail below with reference to production examples of the titanium phosphate powder shown below.

Production Examples 1 to 11 shown in Table 1 are examples where titanium phosphate powders each including hexagonal plate-shaped crystalline particles of titanium phosphate were produced by causing titanium(IV) sulfate and phosphoric acid to react with each other by a hydrothermal synthesis method.

The hydrothermal synthesis method is described in detail. First, titanium(IV) sulfate as a titanium source and phosphoric acid as a phosphorus source were mixed to obtain a mixture, and the mixture was then heated at a predetermined temperature to cause hydrothermal synthesis. The pressurization at this time was natural pressurization. The concentration of titanium in the mixture of titanium(IV) sulfate and phosphoric acid was 0.2 mol/L or more and 0.6 mol/L or less. After the reaction was performed for a predetermined period of time, a slurry-like product was cooled and cleaned with water to obtain a titanium phosphate powder.

TABLE 1

| Prod. Ex. | Concentration of titanium (mol/L) | Concentration of phosphorous (mol/L) | Concentration ratio ([P]/[Ti]) | Reaction temperature (° C.) | Reaction time (h) | Average primary particle diameter (µm) | Average thickness (µm) | Aspect ratio |
|---|---|---|---|---|---|---|---|---|
| 1 | 0.30 | 3.96 | 13 | 160 | 5 | 0.35 | 0.048 | 7 |
| 2 | 0.30 | 3.96 | 13 | 110 | 5 | 0.24 | 0.017 | 14 |
| 3 | 0.30 | 3.96 | 13 | 100 | 5 | 0.21 | 0.019 | 11 |
| 4 | 0.22 | 3.27 | 15 | 160 | 5 | 1.33 | 0.099 | 13 |
| 5 | 0.22 | 4.55 | 21 | 160 | 5 | 0.24 | 0.026 | 9 |
| 6 | 0.26 | 4.29 | 17 | 130 | 5 | 0.19 | 0.025 | 8 |
| 7 | 0.39 | 5.24 | 13 | 110 | 5 | 0.12 | 0.014 | 9 |
| 8 | 0.45 | 6.08 | 14 | 110 | 5 | 0.078 | 0.012 | 7 |
| 9 | 0.58 | 7.75 | 13 | 110 | 5 | 0.072 | 0.014 | 5 |
| 10 | 0.60 | 3.32 | 6 | 110 | 5 | 0.886 | 0.084 | 11 |
| 11 | 0.60 | 2.58 | 4 | 110 | 5 | — | — | — |

The concentration of titanium (by mole) [Ti] and the concentration of phosphorus (by mole) [P] in each mixture of titanium(IV) sulfate and phosphoric acid and each concentration ratio [P]/[Ti] are as shown in Table 1. Each reaction temperature and each reaction time in the hydrothermal synthesis method are also shown in Table 1.

The average primary particle diameter and the average thickness of each of the obtained titanium phosphate powders of Production Examples 1 to 11 were measured, and the aspect ratio was calculated from these numerical values. The average primary particle diameter was obtained by analyzing an image obtained by a scanning electron microscope using an image analysis software Mac-View ver. 4 manufactured by MOUNTECH Co. Ltd. Table 1 summarizes the results obtained.

Figure 2:
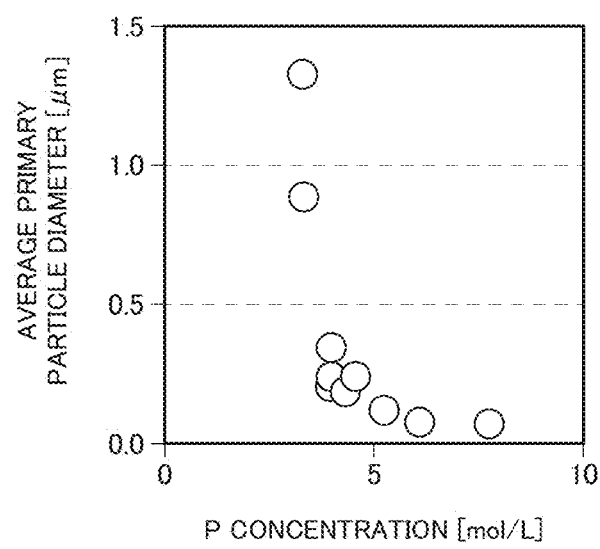
FIG. 2 is a graph illustrating a relationship between the concentration of phosphorus in a mixture of titanium(IV) sulfate and phosphoric acid and the average primary particle diameter of hexagonal plate-shaped crystalline particles of titanium phosphate, obtained from the results of Production Examples 1 to 10.
Figure 3:
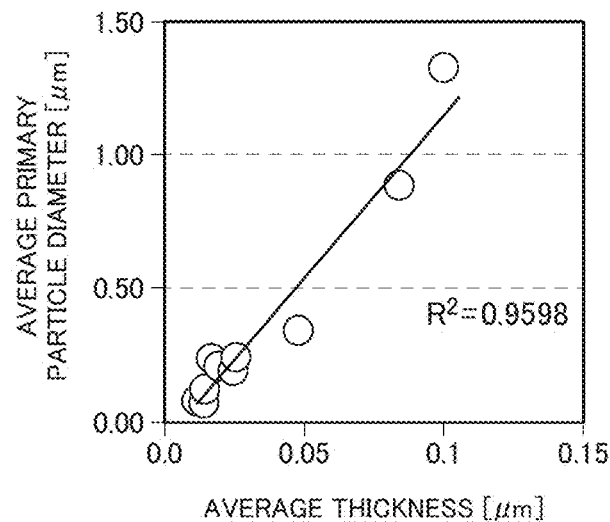
FIG. 3 is a graph illustrating a relationship between the average thickness and the average primary particle diameter of hexagonal plate-shaped crystalline particles of titanium phosphate, obtained from the results of Production Examples 1 to 10.
Figure 4:
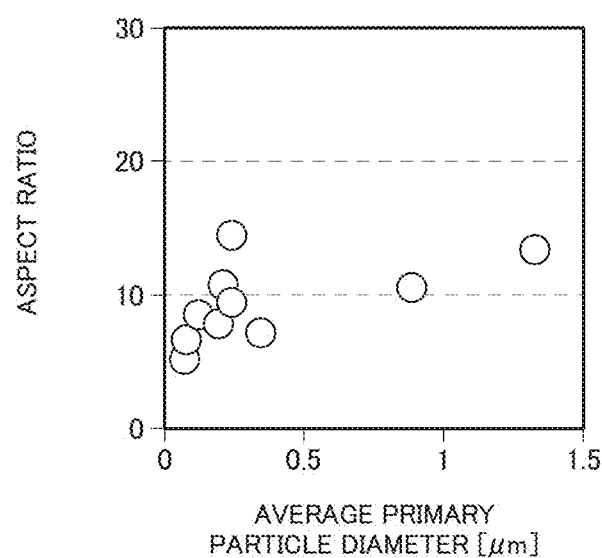
FIG. 4 is a graph illustrating a relationship between the average primary particle diameter and the aspect ratio of hexagonal plate-shaped crystalline particles of titanium phosphate, obtained from the results of Production Examples 1 to 10.

A relationship between the concentration of phosphorus in the mixture of titanium(IV) sulfate and phosphoric acid and the average thickness of hexagonal plate-shaped crystalline particles of titanium phosphate, obtained from the results of Production Examples 1 to 10, is shown in the graph of FIG. 1. A relationship between the concentration of phosphorus in a mixture of titanium(IV) sulfate and phosphoric acid and the average primary particle diameter of hexagonal plate-shaped crystalline particles of titanium phosphate, obtained from these results, is shown in the graph of FIG. 2. A relationship between the average thickness and the average primary particle diameter of hexagonal plate-shaped crystalline particles of titanium phosphate, obtained from the results shown in Table 1, is shown in the graph of FIG. 3. A relationship between the average primary particle diameter and the aspect ratio of hexagonal plate-shaped crystalline particles of titanium phosphate, obtained from the results shown in Table 1, is shown in the graph of FIG. 4.

(Concentration of Titanium)

Each titanium phosphate powder was produced by a hydrothermal synthesis method under the conditions where the concentration ratio [P]/[Ti] was constant (16.5) and the concentration of titanium was 0.22 mol/L or 0.26 mol/L. The reaction temperature was 110° C., 120° C., 130° C., or 160° C.

The results demonstrate that the higher the concentration of titanium is, the smaller the average primary particle diameter of the plate-shaped crystalline particles of titanium phosphate is.

Subsequently, each titanium phosphate powder was produced by a hydrothermal synthesis method under the conditions where the concentration ratio [P]/[Ti] was constant (13.4) and the concentration of titanium was 0.39 mol/L, 0.45 mol/L, 0.52 mol/L, or 0.58 mol/L. The reaction temperature was set to be constant (110° C.)

Figure 5:
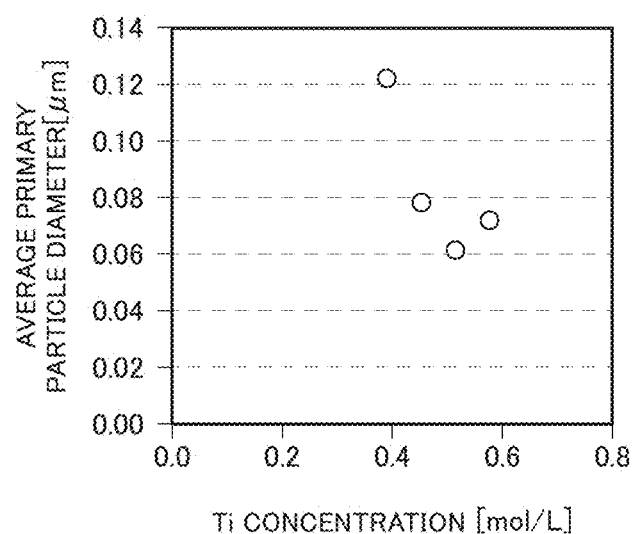
FIG. 5 is a graph illustrating a relationship between the concentration of titanium in a mixture of titanium(IV) sulfate and phosphoric acid and the average primary particle diameter of hexagonal plate-shaped crystalline particles of titanium phosphate, obtained from a production experiment.

The results demonstrate that the higher the concentration of titanium is, the lower the production cost is. A relationship between the concentration of titanium and the average primary particle diameter of the obtained plate-shaped crystalline particles of titanium phosphate is shown in the graph of FIG. 5. As can be seen from this graph, the higher the concentration of titanium is, the smaller the average primary particle diameter of the plate-shaped crystalline particles of titanium phosphate is.

These results demonstrate that the average primary particle diameter of the plate-shaped crystalline particles of titanium phosphate can be controlled to a desired size by reducing the concentration of phosphorus and increasing the concentration of titanium.

(Concentration of Phosphorus)

The effect of the concentration of phosphorus in the case where the concentration of titanium is high (e.g., 0.4 mol/L or more) was examined. Each titanium phosphate powder was produced by a hydrothermal synthesis method under the conditions where the concentration of titanium was 0.22 mol/L, 0.41 mol/L, or 0.60 mol/L and the concentration ratio [P]/[Ti] and the concentration of phosphorus were changed variously. The reaction temperature was 160° C. when the concentration of titanium was 0.22 mol/L, and the reaction temperature was 110° C. when the concentration of titanium was 0.41 mol/L and 0.60 mol/L.

As a result, at any concentration of titanium, when the concentration of phosphorus was 2.6 mol/L or less, the crystallinity of titanium phosphate was reduced, and plate-shaped crystalline particles were not formed, but when the concentration of phosphorus was 3.3 mol/L or more, the plate-shaped crystalline particles of titanium phosphate were formed. Similar to the case where the concentration of titanium was low (e.g., 0.2 mol/L), the average primary particle diameter of plate-shaped crystalline particles of titanium phosphate tended to be smaller as the concentration of phosphorus was higher.

In addition, the results of the examination under the conditions where the concentration of titanium was constant (0.60 mol/L) and the concentration of phosphorus was changed variously (3.3, 4.09, 4.91 mol/L) demonstrate that the average primary particle diameter of the plate-shaped crystalline particles of titanium phosphate changes depending on the concentration of phosphorus.

Figure 6:
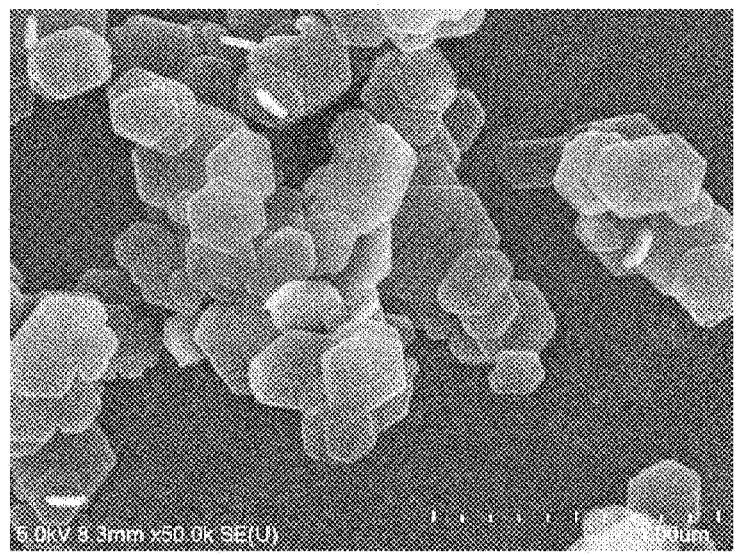
FIG. 6 is an SEM image of a titanium phosphate powder of Production Example 2.
Figure 7:
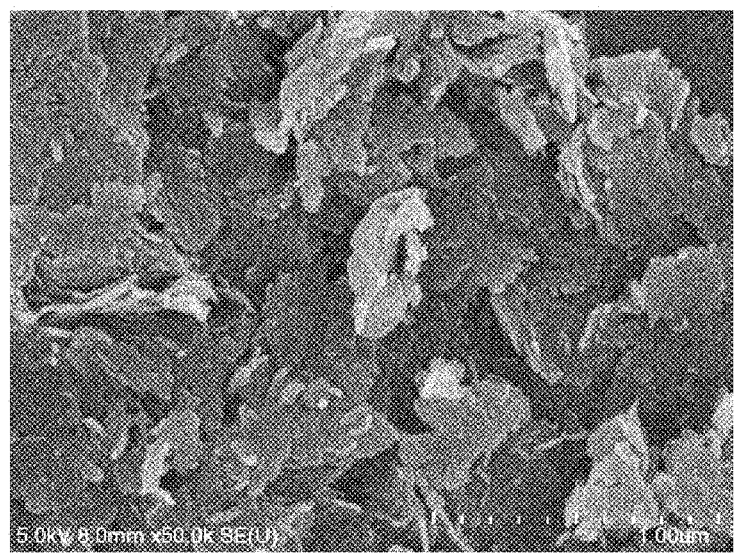
FIG. 7 is an SEM image of a titanium phosphate powder of Production Example 11.

FIG. 6 is an SEM image of the titanium phosphate powder obtained in Production Example 2, and FIG. 7 is an SEM image of the titanium phosphate powder obtained in Production Example 11 corresponding to the comparative example. As can be seen from FIGS. 6 and 7, each of the particles constituting the titanium phosphate powder obtained in Production Example 2 has a hexagonal plate shape, while each of the particles constituting the titanium phosphate powder obtained in Production Example 11 does not have a plate shape but has a rod shape.

The invention claimed is:

1. A method for producing a titanium phosphate powder comprising plate-shaped crystalline particles of titanium phosphate, the method comprising
causing a raw material containing titanium and phosphorus to react by a hydrothermal synthesis method,
wherein:
a mixture of titanium sulfate and phosphoric acid is used as the raw material;
the plate-shaped crystalline particles have an average thickness of 0.01 µm or more and 0.048 µm or less;
the plate-shaped crystalline particles have an aspect ratio that is a value obtained by dividing an average primary particle diameter of the plate-shaped crystalline particles by the average thickness of 7 or more; and
the plate-shaped crystalline particles have an average primary particle diameter of 0.05 µm or more and 0.24 µm or less.

2. The method for producing a titanium phosphate powder according to claim 1, wherein the plate-shaped crystalline particles have an average primary particle diameter of 0.05 µm or more and 0.21 µm or less.

3. The method for producing a titanium phosphate powder according to claim 2, wherein the plate-shaped crystalline particles are hexagonal plate-shaped crystalline particles.

4. The method for producing a titanium phosphate powder according to claim 2, wherein a reaction temperature in the hydrothermal synthesis method is set to 100° C. or more and 160° C. or less.

5. The method for producing a titanium phosphate powder according to claim 2, wherein a ratio ([P]/[Ti]) of a concentration [P] of the phosphorus by mole to a concentration [Ti] of the titanium by mole in the raw material is set to be 5 or more and 21 or less.

6. The method for producing a titanium phosphate powder according to claim 2, wherein a concentration of the titanium in the raw material is set to be 0.2 mol/L or more and 0.6 mol/L or less.

7. The method for producing a titanium phosphate powder according to claim 1, wherein the plate-shaped crystalline particles are hexagonal plate-shaped crystalline particles.

8. The method for producing a titanium phosphate powder according to claim 7, wherein a reaction temperature in the hydrothermal synthesis method is set to 100° C. or more and 160° C. or less.

9. The method for producing a titanium phosphate powder according to claim 7, wherein a ratio ([P]/[Ti]) of a concentration [P] of the phosphorus by mole to a concentration [Ti] of the titanium by mole in the raw material is set to be 5 or more and 21 or less.

10. The method for producing a titanium phosphate powder according to claim 7, wherein a concentration of the titanium in the raw material is set to be 0.2 mol/L or more and 0.6 mol/L or less.

11. The method for producing a titanium phosphate powder according to claim 1, wherein a reaction temperature in the hydrothermal synthesis method is set to 100° C. or more and 160° C. or less.

12. The method for producing a titanium phosphate powder according to claim 11, wherein a ratio ([P]/[Ti]) of a concentration [P] of the phosphorus by mole to a concentration [Ti] of the titanium by mole in the raw material is set to be 5 or more and 21 or less.

13. The method for producing a titanium phosphate powder according to claim 1, wherein a ratio ([P]/[Ti]) of a concentration [P] of the phosphorus by mole to a concentration [Ti] of the titanium by mole in the raw material is set to be 5 or more and 21 or less.

14. The method for producing a titanium phosphate powder according to claim 1, wherein a concentration of the titanium in the raw material is set to be 0.2 mol/L or more and 0.6 mol/L or less.

15. The method for producing a titanium phosphate powder according to claim 1, wherein the plate-shaped crystalline particles have an average primary particle diameter of 0.05 µm or more and 0.19 µm or less.

\* \* \* \* \*